United States Patent [19]
Blum et al.

[11] Patent Number: 5,427,687
[45] Date of Patent: Jun. 27, 1995

[54] BUBBLE REACTION USING VAPOR PERMEATION

[75] Inventors: Stephan Blum, Langenfeld; Bernhard Gutsche; Lutz Jeromin, both of Hilden; Levent Yueksel, Duesseldorf, all of Germany

[73] Assignee: Henkel Kommanditgesellschaft auf Aktien, Duesseldorf, Germany

[21] Appl. No.: 960,459

[22] PCT Filed: Jun. 6, 1991

[86] PCT No.: PCT/EP91/01050
§ 371 Date: Dec. 15, 1992
§ 102(e) Date: Dec. 15, 1992

[87] PCT Pub. No.: WO91/19559
PCT Pub. Date: Dec. 26, 1991

[30] Foreign Application Priority Data
Jun. 15, 1990 [DE] Germany .......... 40 19 170.2

[51] Int. Cl.$^6$ ............................. B01D 61/36
[52] U.S. Cl. ..................... 210/638; 210/640
[58] Field of Search .......... 210/640, 195.2, 192, 210/638

[56] References Cited
U.S. PATENT DOCUMENTS

| | | | |
|---|---|---|---|
| 2,956,070 | 10/1960 | Jennings et al. | 260/410.9 |
| 3,182,043 | 5/1965 | Kirkland | 210/640 X |
| 3,750,735 | 8/1973 | Chiang et al. | 210/640 X |
| 4,755,299 | 7/1988 | Bruschke . | |
| 4,900,402 | 2/1990 | Kaschemekat . | |
| 4,915,834 | 4/1990 | Bruschke . | |

FOREIGN PATENT DOCUMENTS

| | | |
|---|---|---|
| 0009385 | 2/1980 | European Pat. Off. . |
| 0210055 | 1/1987 | European Pat. Off. . |
| 0273267 | 6/1988 | European Pat. Off. . |
| 0294827 | 12/1988 | European Pat. Off. . |
| 0924689 | 5/1955 | Germany . |
| 3220570 | 1/1983 | Germany . |
| 3134539 | 3/1983 | Germany . |
| 3610011 | 1/1989 | Germany . |
| 62-96453 | 10/1987 | Japan . |

OTHER PUBLICATIONS

Chemistry Letters, "The Esterification of Oleic Acid with Ethanol Accompanied by Membrane Separation", Kita, et al., pp. 2053–2056, 1987.
Rautenbach et al. in Chem. Ing. Techn, 61 (1989), pp. 535–544.
G. F. Tusel et al., ACS Symposium Series 281 (1985), Reverse Osmosis and Ultrafiltration, S. Sourirajan (Ed.) 467–478.

Primary Examiner—Frank Spear
Attorney, Agent, or Firm—Ernest G. Szoke; Wayne C. Jaeschke; Henry E. Millson, Jr.

[57] ABSTRACT

Process for carrying out an equilibrium reaction in which one or more products are separated off by vapor permeation comprising the steps of:
- A) forming a reaction mixture comprising the reactants to be reacted in at least one reaction zone at a reaction temperature and reaction pressure selected so as to provide a reaction temperature above the boiling temperature of at least the product or products to be removed, wherein at least the product or products to be removed enters the resulting vapor phase in vapor form;
- B) passing the vapor phase containing the product or products to be removed to a zone remote from the reaction zone, which remote zone contains a semipermeable membrane permeable to the product or products to be removed;
- C) carrying out vapor permeation in said remote zone to remove at least a portion of the product or products to be removed from said vapor phase; and
- D) returning the resulting vapor retentate from step C) to a reaction zone in step A). The process is especially useful in carrying out esterification reaction between a carboxylic acid and an alcohol.

18 Claims, 3 Drawing Sheets

BUBBLE REACTION USING VAPOR PERMEATION

BACKGROUND OF THE INVENTION

1. Field of the Invention

This invention relates to a process for conducting an equilibrium reaction in which one or more products is/are separated off by vapor permeation. More particularly, the invention relates to a process for conducting an esterification reaction in which water vapor is removed by vapor permeation.

2. Statement of Related Art

Membrane processes for the fractionation of mixtures containing organic components are described in detail in the literature, cf. for example Rautenbach et al. in Chem. Ing. Techn. 61 (1989), pages 535–544. The use of pervaporation and vapor permeation is also described in the prior art literature, cf. DE 3 610 011 C2, EP 0 294 827 A2 and EP 0 273 267 A2.

In these processes, the mixture to be separated (feed) is generally guided along a membrane which is permeable to one component (semi-permeable). A vacuum applied to the feed-remote side (permeate side) of the membrane produces a potential gradient which results in removal of the predominantly permeating component from the feed. The stripped feed is called the retentate or concentrate. The substantially pure component separated by the membrane is called the permeate. The separation behavior of the membrane is very much dependent on temperature, although an upper limit is imposed by thermal stability. For example, the GFT standard membrane is said to have a maximum thermal stability of 130° C. (G. F. Tusel et al., ACS Symposium Series 281 (1985), Reverse Osmosis and Ultrafiltration, S. Sourirajan (Ed.) 467–478). However, there is still no evidence of long-term stability above 100° C. On the basis of operating experience, the optimal separation behavior of the GFT standard membrane is between 80° C. and 100° C.

The processes described in DE 3 610 011 C2 and EP 0 294 827 A2 are distinguished by the fact that the feed is introduced in liquid form just below its boiling point under the prevailing system pressure. The system pressure has to be selected so that the temperature of the feed at the membrane corresponds to the optimal temperature and is never above the maximum temperature because the membrane would otherwise be irreversibly damaged.

In addition, the contact of the feed with hydrophilic membranes (GFT standard membranes) results in swelling of the active layer which, in turn, causes an increase in permeability on the one hand, but a loss of selectivity on the other hand. With high water contents and high temperatures, this swelling can lead to separation of the active layer from its backing cloth and, hence, to destruction of the membrane. In addition, there must be no danger of chemical damage to the membrane by any one of the feed components.

Accordingly, the use of pervaporation in reactions is seriously limited.

The process of vapor permeation is described in EP 0 273 267 A2. Vapor permeation is distinguished from pervaporation by the fact that the feed is evaporated and the vapor is guided along the membrane. In this case, too, the system pressure has to be selected so that the vapor temperature and hence the temperature of the feed correspond to the optimal temperature of the membrane. In vapor permeation, too, the boiling temperature of the feed must not exceed the maximum temperature of the membrane.

Vapor permeation has the advantage over pervaporation that, on the one hand, the membrane does not swell and, on the other hand, the danger of chemical damage to the membrane is largely ruled out.

U.S. Pat. No. 2,956,070 and EP 0 210 055 A1 are concerned with the removal of water during esterification reactions by pervaporation.

For the reasons explained above, pervaporation is carried out at moderate reaction temperatures (50°–90° C.) in the tests mentioned in EP 0 210 055 A1. In this case, reference is made to the low acid resistance of the membranes (max. 15 mol-% of the reaction mixture) which causes a large excess of alcohol.

A process for using vapor permeation for the removal of water in the esterification of oleic acid with ethanol is described in Kita et al., Chem. Letters (1987), No. 10, pp. 2053–2056. In this case, the tests were carried out at moderate temperatures (85° C.). In the test arrangement used, the reaction temperature again must not exceed the maximum temperature of the membrane for the reasons explained above.

DESCRIPTION OF THE INVENTION

The disadvantage of all the processes mentioned above is that the fatty acid and the alcohol are introduced in admixture. The system pressure always has to be adjusted so that the boiling temperature of the mixture is equal to the temperature required for the reaction. For the reasons explained above, however, this temperature must not exceed the maximum temperature of the membrane (100° C. in the case of the GFT standard membrane). However, most of the reaction temperatures are distinctly above 100° C. so that the maximum temperatures of most membranes are far exceeded. In the above-mentioned processes, therefore, the removal of water during esterification reactions can be carried out at best at the maximum temperature of the membrane used although this does result in reaction times that are longer; the higher the optimal reaction temperature is above that maximum temperature.

The problem addressed by the present invention was to obtain high reaction rates in the process mentioned at the beginning by a special method of conducting equilibrium reactions, for example esterification reactions, at high reaction temperatures (>120° C.). The reaction would be able to take place at any temperatures. In addition, the membrane would not have to have above-average chemical stability, even in the presence of strong solvents in the feed, i.e. the acid could be introduced in pure form. This would enable the conduct of the reaction to be freely adapted to the optimal membrane temperature.

According to the invention, the solution to this problem is characterized in that the reaction is carried out in a bubble reactor and the lower-boiling educt is passed through the educt initially introduced which is kept at the reaction temperature, the reaction temperature and the reactor pressure being adjusted so that the reaction temperature is above the boiling temperature of at least one of the products; in that the vapor permeation is carried out outside the reactor at a suitable temperature which is dependent on the membrane material and in that the vapor phase of the reaction mixture in the reactor is delivered as feed to the membrane module in which the vapor permeation is to be carried out. The only requirements to be satisfied in this regard are that at least the product to be separated should enter the vapor phase, the vapor permeation should be carried out in a separate module, optionally at another temperature, and that the vapor phase should be delivered as feed to the membrane module used to carry out the vapor permeation. The feed may be the vapor phase of the reaction mixture or the reaction mixture itself. Mass transport is critically determined by the partial pressure difference which can be achieved both by application of a vacuum on the permeate side and by operation under pressure on the feed side.

The use of the bubble reactor surmounted by a vapor permeation module has the advantage that there are no longer any process restrictions. The only requirement for the reaction is that at least the product component to be removed must be present in vapor form at the reaction temperature. This can always be guaranteed simply by predetermination of the system pressure. The educts or the products may represent both the higher-boiling components and the lower-boiling components. The unrestricted conduct of the reaction is made possible by the fact that, on the one hand, both educts can be separately introduced through the use of the bubble reactor and, hence, the temperature of the reaction vapor mixture accumulating can be freely adjusted, irrespective of the reaction temperature, through predetermination of the system pressure. Secondly, through the use of vapor permeation, the reaction can take place both in the liquid phase and in the vapor phase, irrespective of whether the component to be separated is the main product, a secondary product or the sole product. Thirdly, liquid phase contact between the membrane and a membrane-damaging component is avoided through the use of vapor permeation.

A typical example is the esterification of a fatty acid with a lower-boiling alcohol. As described above, the fatty acid and the alcohol are separately introduced.

Two effects are used for the separation of product—water in the example in question. Firstly, on account of the high temperature of the educt initially introduced (acid in the example), the reaction product to be separated passes into the vapor phase immediately after formation and evaporates from the reaction volume. Secondly, the product to be separated (water) is desorbed from the reaction mixture by the circulating retentate vapor (alcohol/water vapor mixture)., i.e. the reaction product to be separated is thus additionally stripped out by the retentate bubbling through.

This conduct of the reaction provides on the one hand for a further reduction in the amounts of energy and materials to be used and, on the other hand, for a reduction in the batch and reaction times. More particularly, stoichiometric quantities of the educts can be reacted in short reaction times (Example I, Table 2).

To obtain both an optimal reactor temperature and an optimal membrane temperature, although these temperatures generally differ from one another, the membrane module and/or its feed pipe coming from the reactor is heated or cooled in dependence upon the desired membrane temperature.

In the latter case, the vapor may be directly cooled by evaporative cooling (blowing in of liquid alcohol) to avoid cooling of the module. However, this measure leads to a reduction in the partial pressure of the predominantly permeating component and, hence, to a reduction in the driving force.

According to the invention, the reactor is in the form of a bubble reactor in which, in the example of esterification, the fatty acid is brought to the necessary reaction temperature. The alcohol is pumped into the reactor in liquid form close to its boiling point.

Since the reaction temperature is (distinctly) above the boiling temperature of the alcohol, the alcohol suddenly evaporates on entering the hot acid, passes through the reaction volume in bubble form and thus provides for thorough mixing. The water formed by the reaction escapes with the unreacted alcohol into the vapor space as a super-heated vapor mixture. The vapor mixture is fed to a membrane module which is used to accommodate the membrane. The water in this vaporous alcohol/water mixture is removed by the vacuum applied to the permeate side of the membrane. The remaining retentate, which consists of unreacted alcohol and unseparated water, is optionally condensed and returned to the reaction mixture.

Accordingly, the retentate formed during vapor permeation is returned to the reactor. More particularly, the retentate is introduced into the reactor in liquid form with the lower-boiling educt.

In another advantageous embodiment of the invention, the retentate is introduced into the reactor in gaseous form together with the lower-boiling educt (FIG. 2). In the case of esterification, the alcohol/water mixture is blown into the reactor in gaseous form. The vapor stream issuing from the reactor is passed through the membrane module, as in the above-described conduct of the reaction, and is then taken in again under suction. This recirculation eliminates the need for energy-intensive evaporation and, hence, for subsequent condensation of the retentate.

Other design solutions are also possible. Thus, through a special design of the reactor, there is no need whatever for the units for maintaining the vapor circulation, such as pumps and compressors for example.

In one particularly advantageous embodiment for working on an industrial scale, the higher-boiling educt and the lower-boiling educt are passed in countercurrent through a cascade of stirred tanks (FIG. 3) and the gas phase of the reaction mixture is only delivered to the membrane module after passing through the cascade. The membrane area required is thus minimized. In another advantageous embodiment, the educts are passed through a countercurrent column and the gaseous reaction product formed is delivered to the membrane module. In this case, too, only a small membrane surface is necessary.

In order to keep any small quantities of membrane-damaging educt or product present in the vapor, for example acid or ester in the esterification process, away from the membrane, it is of advantage to pass the vapors through a suitable unit, for example a preceding drop separator, before the feed pipe to the membrane module in order to remove entrained liquid.

Some examples of embodiment of the invention are described in detail in the following with reference to the accompanying drawings, wherein.

Figure 1:
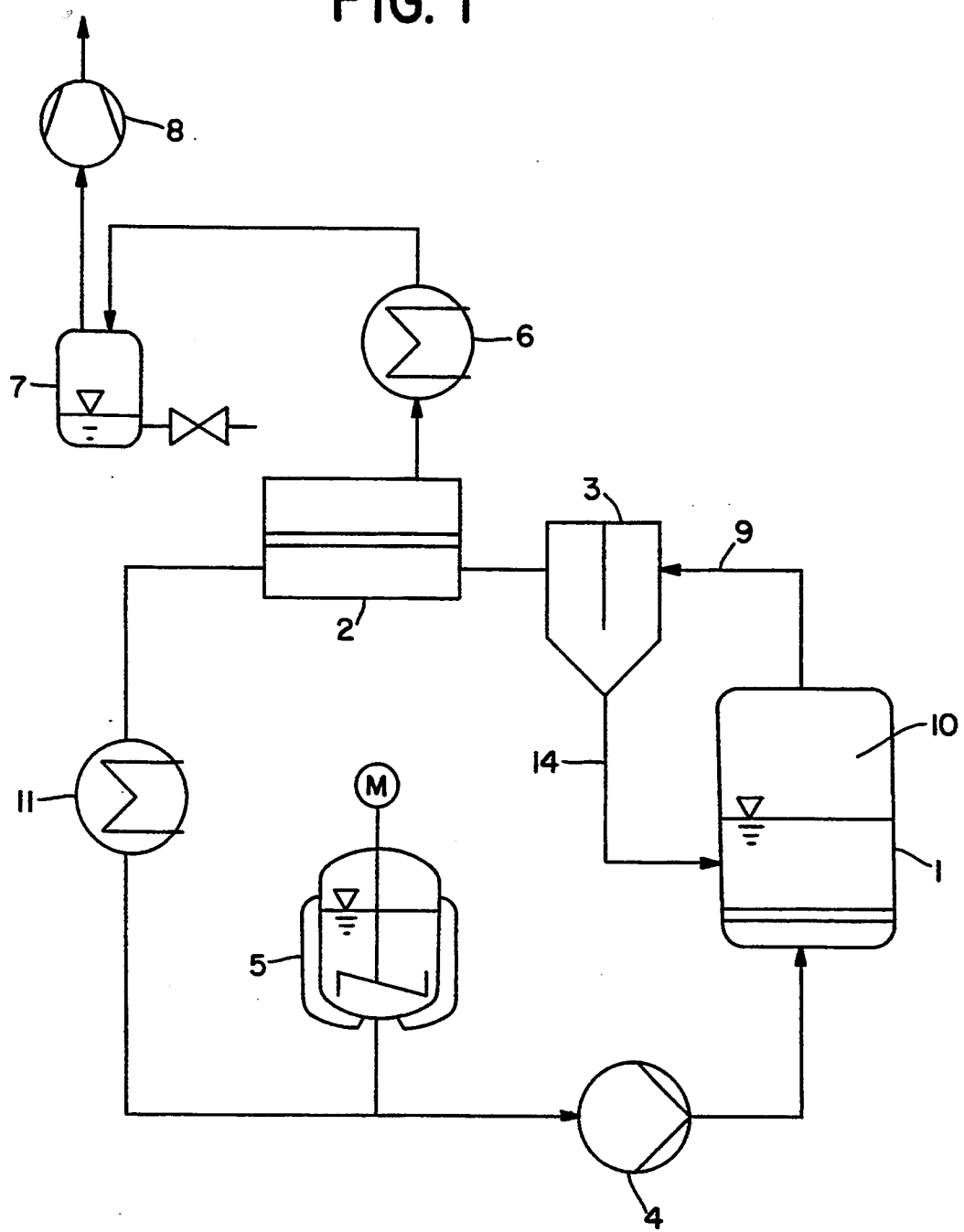
FIG. 1 is a flow chart of an esterification process according to the invention in which the retentate is pumped into the reactor in liquid form.

The embodiment shown by way of example in FIG. 1 relates to an esterification reaction. The pump 4 pumps the alcohol in liquid form from a separate storage container 5 into the bubble reactor I at a temperature close to its boiling point. In this reactor, fatty acid is kept at the necessary reaction temperature. On entering the hot fatty acid, the alcohol suddenly evaporates, bubbles through the reaction mixture and thus provides for thorough mixing. The water formed by the reaction escapes into the vapor space with the unreacted alcohol in the form of a superheated vapor mixture, the vapor phase 10. A feed pipe 9 leads from the vapor space of the reactor 1 to a membrane module 2 via a drop separator 3. The membrane module 2 accommodates the membrane. The water in the vaporous alcohol/water mixture passing along the membrane is removed by the vacuum applied to the permeate side of the membrane from the vacuum source 8. The remaining retentate consists of unreacted alcohol and unseparated water and is condensed in the condenser 11 by a stream of suitable refrigerant and returned to the reaction mixture in the reactor 1. After condensation at the permeate condenser 6, the permeate is collected in the permeate collecting tank 7.

Figure 2:
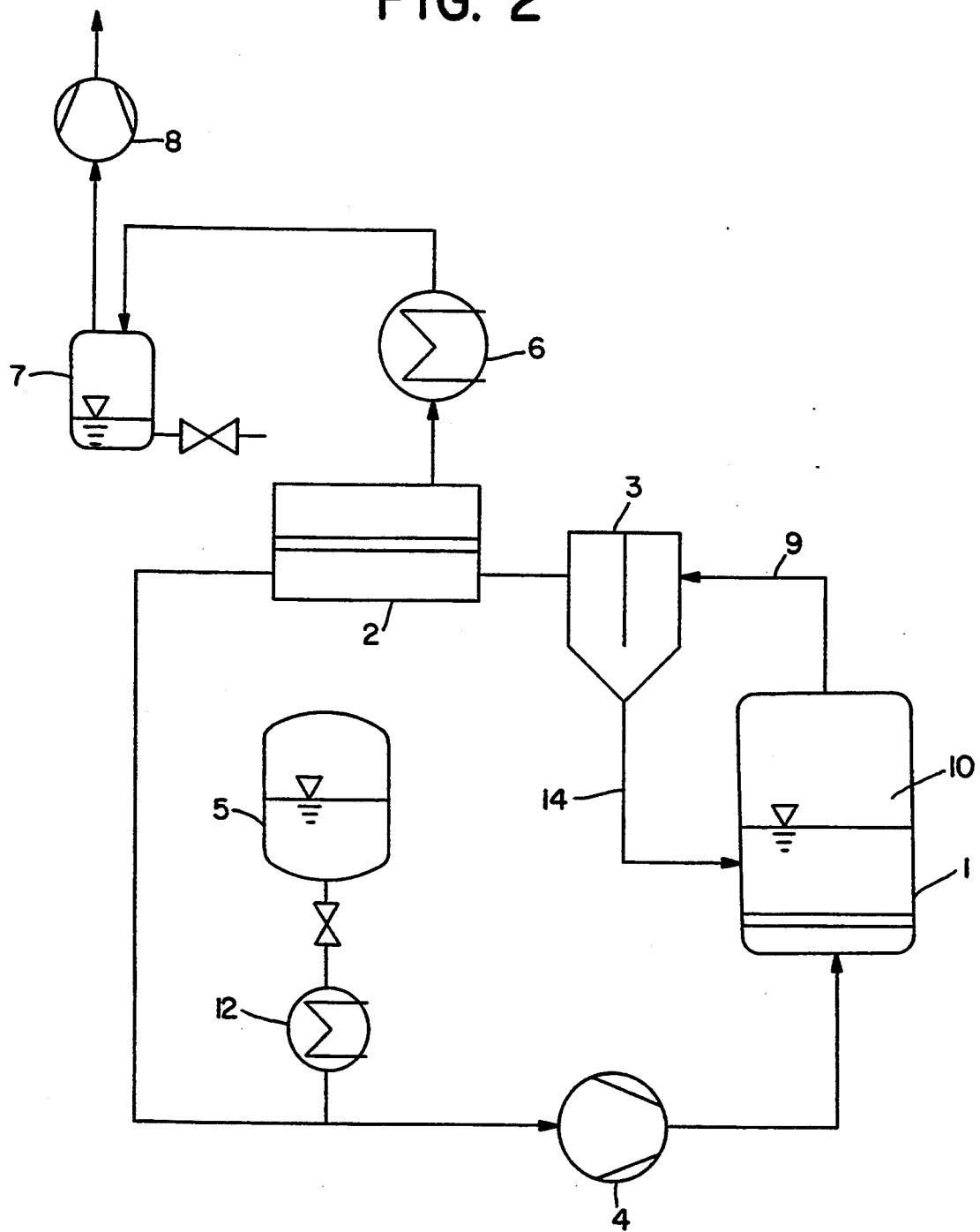
FIG. 2 is a flow chart corresponding to FIG. 1, except that the retentate is delivered to the reactor in gaseous form.

The embodiment shown in FIG. 2 corresponds to that shown in FIG. 1 except that the alcohol/water mixture is blown into the reactor 1 in gaseous formed by the gas compressor 4. The stream of vapor issuing from the reactor 1 is passed through the membrane module 2 and then taken in again by the gas compressor 4. The advantage of this embodiment is that it eliminates the need for energy-intensive evaporation and, hence, subsequent condensation of the retentate.

Figure 3:
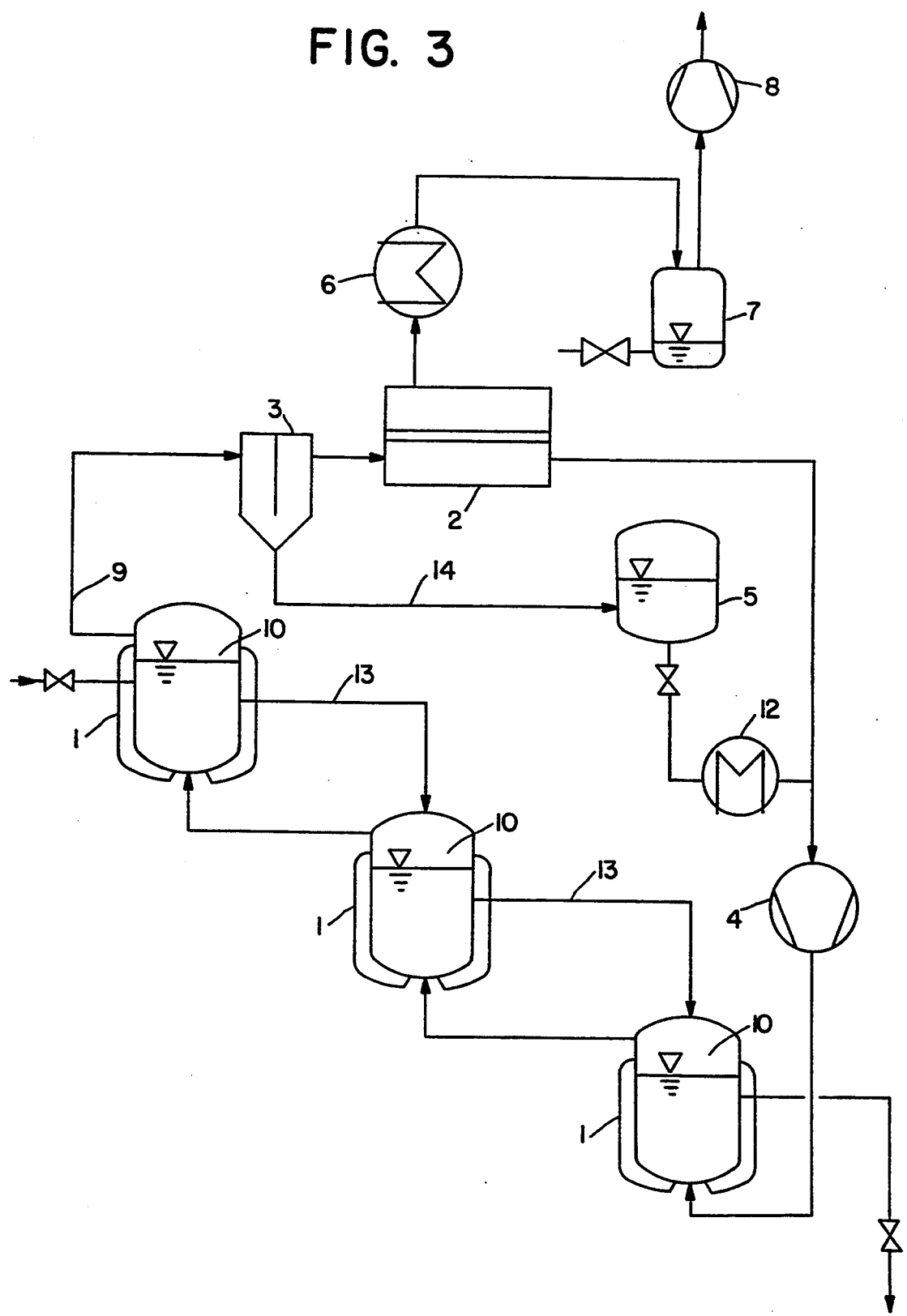
FIG. 3 shows an embodiment of the invention comprising a cascade of stirred tanks operated in countercurrent.

A flow chart for the industrial-scale operation of the process according to the invention is shown in FIG. 3. The reaction is carried out in several reactors 1 operated as a cascade of stirred tank reactors in countercurrent to the circulating vapor mixture. Both continuous and discontinuous operation are possible. The vapor mixture issuing from the last reactor, which is enriched with the predominantly permeating material, is deconcentrated in the membrane module 2 and returned to the first reactor 1. This embodiment otherwise corresponds to the embodiment shown in FIG. 2.

EXAMPLE I

The results of an esterification reaction of myristic acid with isopropanol (IPA) to isopropyl myristate (IPM) and water carried out by the process according to the invention are presented in the following.

The bubble reactor used was a glass reactor having a reaction volume of 0.6 l (starting quantity mole myristic acid = 2 mol). The GFT standard membrane with an area, based on the reaction volume, of 115.5 m$^2$/m$^3$ IPM, was installed in a module surmounting the reactor. This membrane is a two-layer composite membrane having an active layer of crosslinked polyvinyl alcohol (PVA) and a protective layer of polyacrylonitrile. The exact construction of the membrane is described in DE 3 220 570 A1. The myristic acid was initially introduced under normal pressure at 120° C. and IPA was subsequently pumped into the hot acid in liquid form at approximately 82° C. The quantity of IPA used was in a molar ratio of 2.45:1 to the myristic acid used.

The reaction was initially carried out without removal of water in order to quantify the mode of operation of the bubble reactor design. The conversion of myristic acid as a function of time is shown in Table 1. The equilibrium conversion of a batch reactor is shown for comparison. The distinctly better conversion in the bubble reactor without removal of water by comparison with the batch reactor is attributable to the stripping effect of the IPA/water mixture.

In addition, the substantially complete conversion of the myristic acid in the bubble reactor with removal of water through the membrane is clearly apparent from Table 1. The corresponding permeate flows are also shown.

TABLE 1

| | Molar ratio 2.45:1 | | |
|---|---|---|---|
| Test duration (h) | Bubble reactor without removal of water Myristic acid conversion | Bubble reactor with removal of water Myristic acid conversion | Spec. flow (kg/m$^2$h) |
| 0.0 | 0 | 0 | — |
| 0.5 | 0.178 | 0.151 | 0.05 |
| 1.0 | 0.398 | 0.369 | 0.175 |
| 1.5 | 0.537 | 0.562 | 0.137 |
| 2.0 | 0.618 | 0.682 | 0.127 |
| 3.0 | 0.710 | 0.845 | 0.100 |
| 4.0 | 0.767 | 0.924 | 0.025 |
| 5.0 | 0.808 | 0.962 | 0.022 |
| 6.0 | 0.833 | 0.975 | 0.011 |
| 7.0 | 0.853 | 0.981 | 0.005 |
| 8.0 | 0.865 | 0.987 | 0.001 |
| 9.0 | 0.877 | | |
| 10.0 | 0.887 | | |
| 11.0 | 0.896 | | |
| 12.0 | 0.904 | | |
| 13.0 | 0.908 | | |
| 14.0 | 0.910 | | |

Equilibrium conversion bubble reactor without removal of water: 0.910
Equilibrium conversion batch reactor without removal of water: 0.808

$$\text{Conversion} = 1 - \frac{\text{mol myristic acid}}{\text{mol}_0 \text{ myristic acid}}$$

In another test, the molar ratio of the educts was also reduced for a specific membrane area of 115.5 m$^2$/m$^3$ myristic acid (Table 2). In contrast to the reaction behavior in the batch reactor, the reaction time in the bubble reactor can be minimized by reduction of the excess of the non-key component in the educt (IPA in the Example). This can be explained by the fact that mostly water of reaction and hardly any IPA enter the vapor phase so that the partial pressure of the water in the vapor and hence the driving force of the permeation are increased.

It can be seen from this that the reaction can be carried out stoichiometrically (molar ratio 1:1). Working up of the product, which always accumulates at relatively high molar ratios, can be minimized in this way or even omitted altogether.

TABLE 2

| Test duration (h) | Conversion bubble reactor with removal of water Molar ratio 2.45:1 Conversion myristic acid | Conversion bubble reactor with removal of water Molar ratio 1.185:1 Conversion myristic acid |
|---|---|---|
| 0.0 | 0 | 0 |
| 0.5 | 0.151 | 0.314 |
| 1.0 | 0.369 | 0.631 |
| 1.5 | 0.562 | 0.839 |
| 2.0 | 0.682 | 0.920 |
| 3.0 | 0.845 | 0.978 |
| 4.0 | 0.924 | 0.993 |
| 5.0 | 0.962 | 0.996 |
| 6.0 | 0.975 | 0.999 |

TABLE 2-continued

| Test duration (h) | Conversion bubble reactor with removal of water Molar ratio 2.45:1 Conversion myristic acid | Conversion bubble reactor with removal of water Molar ratio 1.185:1 Conversion myristic acid |
| --- | --- | --- |
| 7.0 | 0.981 | 1.0 |
| 8.0 | 0.987 | 1.0 |

EXAMPLE II

The esterification of dodecanol and acetic acid to dodecyl acetate and water was investigated in a second Example. An acetic-acid-resistant membrane from GFT was used in this case. The membrane in question is a three-layer composite membrane made up of an active PVA layer on a PAN backing layer applied to a polyester nonwoven. The resistance to acetic acid was obtained by a different form of crosslinking of the PVA layer than in the GFT standard membrane. The exact construction of the membrane is again described in DE 3 220 570 A1. In view of the low boiling temperature of the mixture of 80° C., both educts ($mol_0$ acetic acid =2 mol) were initially introduced in admixture at 80° C. The esterification was carried out at a dodecanol/acetic acid ratio of 1:1.

The reaction was initially carried out without removal of water, i.e. in this case the reactor operated as a batch reactor. In the test with removal of water, a specific membrane area of 12.0 m²/m³ was used.

The acetic acid conversion as a function of time with and without removal of water is shown in Table 3. In this case, too, the complete conversion of the acetic acid by the removal of water is clearly apparent. In addition, the corresponding permeate flows are again shown.

TABLE 3

| Test duration (h) | Batch reactor without removal of water Conversion acetic acid | Batch reactor with removal of water Conversion acetic acid | Spec. flow (kg/m²) |
| --- | --- | --- | --- |
| 0 | 0.0 | 0.0 | — |
| 2 mins. | 0.437 | 0.410 | — |
| 15 mins. | 0.689 | 0.669 | 1.32 |
| 0.5 | 0.736 | 0.745 | 1.43 |
| 1.0 | 0.776 | 0.787 | 1.29 |
| 1.5 | 0.795 | 0.809 | 1.24 |
| 2.0 | 0.801 | 0.839 | 0.97 |
| 4.0 | 0.816 | 0.901 | 0.75 |
| 5.0 | 0.816 | 0.912 | 0.62 |
| 20.0 | 0.816 | 0.972 | 0.035 |
| 49.0 | 0.816 | 0.984 | 0.011 |

Conversion = $1 - \frac{mol\ acetic\ acid}{mol_0\ acetic\ acid}$

We claim:

1. A process for carrying out an equilibrium reaction in which one or more products are separated off by vapor permeation comprising the steps of:

A) forming a reaction mixture comprising a higher boiling and a lower boiling reactant in a bubble reaction zone by first adding the higher boiling reactant to the reaction zone and then passing the lower boiling reactant in bubble form through the higher boiling reactant at a reaction temperature and reaction pressure selected so as to provide a reaction temperature above the boiling temperature of at least the reaction product of products to be removed, wherein at least the reaction product or products to be removed enters the resulting vapor phase in vapor form;

B) passing the vapor phase containing the product or products to be removed to a zone remote from the reaction zone, which remote zone contains a semi-permeable membrane permeable to the product or products to be removed;

C) carrying out vapor permeation in said remote zone to remove at least a portion of the product or products to be removed from said vapor phase at a temperature desired for vapor permeation and different from the reaction temperature; and D) returning the resulting vapor retentate from step C) to the reaction zone in step A).

2. The process of claim 1 wherein the equilibrium reaction is an esterification reaction between a carboxylic acid and an alcohol.

3. The process of claim 2 wherein the carboxylic acid is a fatty acid and the alcohol is a low boiling alkanol.

4. The process of claim 2 wherein the alcohol is introduced into step A in liquid form at a temperature close to its boiling point.

5. The process of claim 2 which the reaction temperature in step A is above 120° C.

6. The process of claim 1 wherein the vapor phase from step A) is heated or cooled to the desired temperature for vapor permeation prior to carrying out step B).

7. The process of claim 1 wherein the vapor retentate in step D) is returned to step A) in liquid form.

8. The process of claim 1 wherein the vapor retentate in step D) is returned to step A) in vapor form.

9. The process of claim 1 wherein entrained liquid is removed from the vapor phase from step A) prior to carrying out step B).

10. The process of claim 1 wherein step C) is carried out by a pressure difference between the two sides of the semi-permeable membrane.

11. The process of claim 10 wherein said pressure difference is achieved by applying a vacuum on the permeate side of the membrane and/or a positive pressure on the vapor feed side of the membrane.

12. The process of claim 1 wherein in step A) a higher-boiling reactant in liquid form and a lower-boiling reactant in vapor form are passed countercurrently through a plurality of reaction zones, and the vapor phase from step A) is removed to a remote zone only after having passed through the plurality of reaction zones.

13. A continuous process for carrying out an equilibrium reaction in which one or more products are separated off by vapor permeation comprising the steps of:

A) passing a reactant in liquid form and a lower-boiling reactant in vapor form countercurrently through a plurality of reaction zones at a reaction temperature and reaction pressure such that the reaction product or products to be removed enters the vapor phase in the form of a vapor;

B) removing the vapor phase containing the product or products to be removed from the last of the reaction zones;

C) removing entrained liquid from the vapor phase and heating or cooling the vapor phase as needed, either before or after removing entrained liquid, to the temperature desired for vapor permeation;

D) passing the vapor phase containing the product or products to be removed to a zone remote from the reaction zone, which remote zone contains a semi-permeable membrane permeable to the product or products to be removed;

E) carrying out vapor permeation in said remote zone to remove at least a portion of the product or products to be removed from said vapor phase; and F) returning the resulting vapor retentate from step E) to a reaction zone in step A).

14. The process of claim 13 wherein step E) is carried out by means of a pressure difference between the two sides of the semi-permeable membrane, said pressure difference being achieved by applying a vacuum on the permeate side of the membrane and/or a positive pressure on vapor feed side of the membrane.

15. The process of claim 13 wherein the vapor retentate in step F) is returned to a reaction zone in step A) in liquid form.

16. The process of claim 13 wherein the vapor retentate phase in step F) is returned to a reaction zone in step A) in vapor form.

17. The process of claim 13 wherein the equilibrium reaction is an esterification reaction between a carboxylic acid and an alcohol.

18. The process of claim 17 wherein the carboxylic acid is a fatty acid and the alcohol is a low boiling alkanol.

* * * * *